US00RE38331E

(19) United States
(12) Reissued Patent
Cameron et al.

(10) Patent Number: US RE38,331 E
(45) Date of Reissued Patent: Nov. 25, 2003

(54) CELLS WITH ALTERED BETAINE CATABOLISM AND THEIR USE IN PRODUCING METABOLITES OR ENZYMES

(75) Inventors: Beatrice Cameron, Paris (FR); Joel Crouzet, Sceaux (FR)

(73) Assignee: Rhone-Poulenc Biochimie, Antony (FR)

(21) Appl. No.: 09/851,950

(22) PCT Filed: Dec. 7, 1993

(86) PCT No.: PCT/FR93/01202

§ 371 (c)(1), (2), (4) Date: May 18, 1995

(87) PCT Pub. No.: WO94/13813

PCT Pub. Date: Jun. 23, 1994

Related U.S. Patent Documents

Reissue of:
(64) Patent No.: 5,691,163
Issued: Nov. 25, 1997
Appl. No.: 08/436,393
Filed: May 18, 1995

(30) Foreign Application Priority Data

Dec. 9, 1992 (FR) ..... 92 14814

(51) Int. Cl.[7] ..... C12P 1/00; C12P 33/02; C12P 21/06; C12N 9/00; C12N 9/02

(52) U.S. Cl. ..... 435/41; 435/69.1; 435/61; 435/86; 435/183; 435/189; 435/190; 435/252.3; 435/253.3

(58) Field of Search ..... 435/41, 86, 253.3, 435/183, 61, 69.1, 440, 189, 190; 431/252.3

(56) References Cited

FOREIGN PATENT DOCUMENTS

WO WO 91/11518 8/1991

OTHER PUBLICATIONS

Kawahara, Y. et al., "*Effect of glycine betaine an osmoprotective compound on the growth of Brevibacterium lactofermentum,*" Appl. Microbiol. Biotechnol., vol. 33, pp. 574–577 (1990).

Lago, B.D. et al., "*Alternate requirement for vitamin B12 or methionine in mutants of Pseudomonas* denitrificans, a vitamin B12–producing bacterium," J. Bact., vol. 99, No. 1, pp. 347–349 (Jul. 1969).

White, R.F. et al., "*Betaine–homocysteine transmethylase in Pseudomonas denitrificans a vitamin B12 overproducer,*" J. Bact., vol. 113, No. 1, pp. 218–223 (1973).

*Primary Examiner*—Ponnathapu Achutamurthy
*Assistant Examiner*—Manjunath N. Rao
(74) *Attorney, Agent, or Firm*—Finnegan, Henderson, Farabow, Garrett & Dunner LLP

(57) ABSTRACT

Cells with an alteration at least in the gene involved in betaine catabolism, their preparation and their use, in particular for producing metabolites and/or enzymes, are disclosed.

25 Claims, 4 Drawing Sheets

Figure 1:
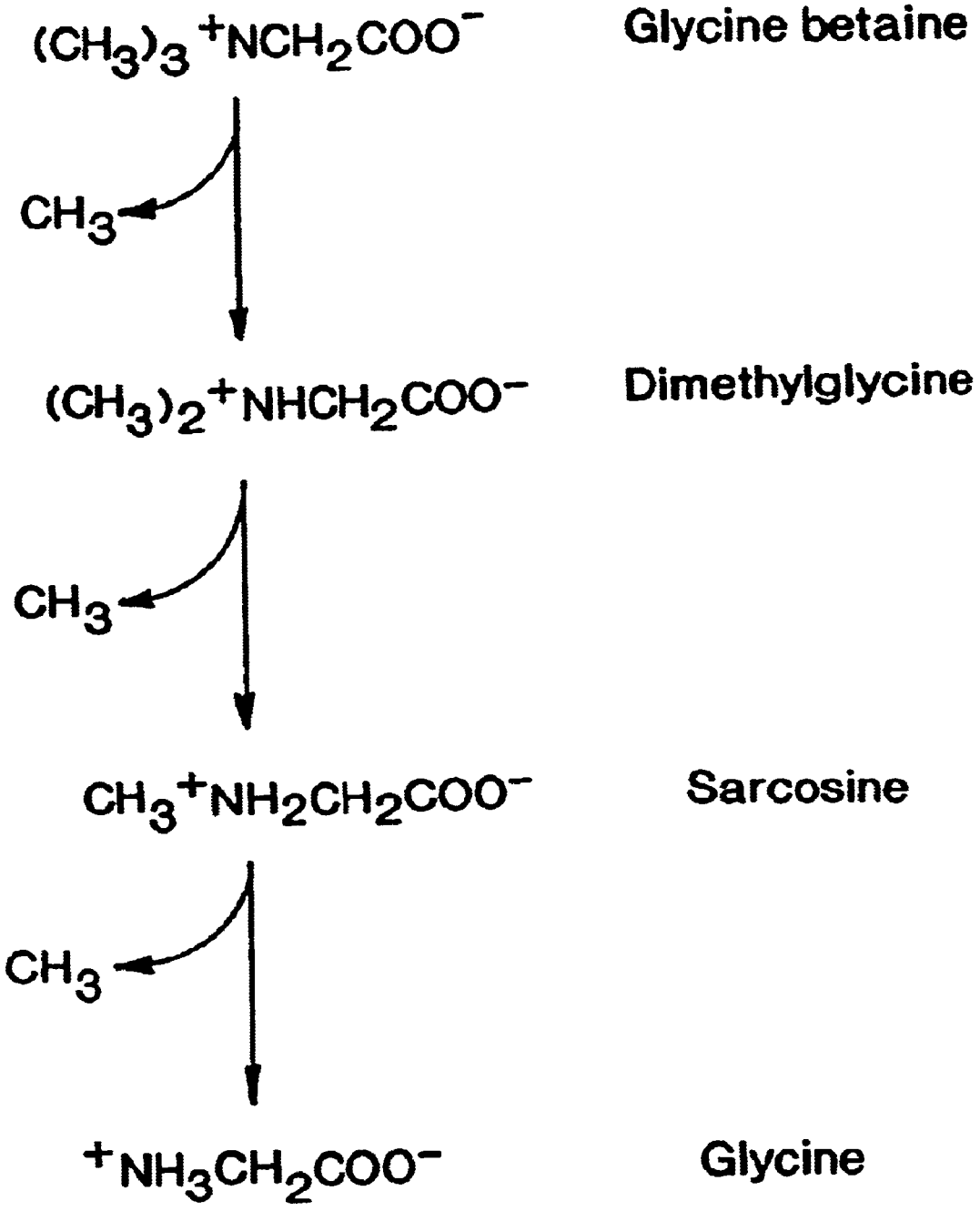

CELLS WITH ALTERED BETAINE CATABOLISM AND THEIR USE IN PRODUCING METABOLITES OR ENZYMES

Matter enclosed in heavy brackets [ ] appears in the original patent but forms no part of this reissue specification; matter printed in italics indicates the additions made by reissue.

This application is a 371 of PCT/FR93/01202 Dec. 7, 1993.

The present invention relates to cells modified with respect to the catabolism of betaine, to their preparation and their use, especially for the improved production of metabolites and/or enzymes. The invention also relates to DNA fragments carrying genes for the catabolism of betaine.

Glycine betaine (N,N,N-trimethylglycine) is generally known for its osmoprotective properties, which confer on bacteria tolerance to osmotic stress (Csonka, 1989). To explain the origin of this property, it has been proposed that the molecular effects of glycine betaine on the activity of water and on the osmotic pressure of the cytoplasm in Escherichia coli were more important than those of the solutes which it replaces (Cayley et al, 1992). Furthermore, in addition to its osmoprotective potentials, it has been described that glycine betaine could also promote the production of enzymes (JP 8,260,709) or of metabolites, such as amino acids (Patent JP 202703); antibiotics (Patent AU 825513) and vitamins (White et al, 1971). However, most bacteria except cyanobacteria and other $CO_2$-fixing prokaryotes do not synthesize glycine betaine which is mainly synthesized by plants. It should therefore be added to production media in fermenters, which generates an additional cost in an industrial process. The present invention provides a solution to this problem.

The applicant has indeed demonstrated that it is possible, by modifying the catabolism of betaine of cells, especially by genetic means, to potentiate the effect of this compound on the production of enzymes or of metabolites without affecting the rate of growth of cells, their viability and the like, under industrial fermentation conditions. The applicant has also identified, isolated and characterized DNA fragments containing genes involved in the catabolism of betaine, which make it possible in particular to prepare cells specifically modified with respect to the catabolism of betaine, and whose modifications are segregationally stable and nonreversible. These fragments also make it possible to stimulate the catabolism of betaine by amplification of the appropriate enzymatic activities. The present invention therefore makes it possible to potentiate the effects of betaine and, thereby, to use this compound economically in industrial fermentation processes.

A first subject of the invention therefore relates to a modified cell exhibiting at least one modification with respect to a gene involved in the catabolism of betaine.

In a first embodiment, the term modified cell designates more particularly any cell having a substitution and/or a deletion and/or an insertion of one or more bases in the considered gene(s) and degrading betaine less rapidly. Such modifications can be obtained in vitro (on isolated DNA fragments carrying genes for the catabolism of betaine) or in situ, for example, by means of genetic engineering techniques, or alternatively by exposing the said cells to a treatment by means of mutagenic agents.

As mutagenic agents, there may be mentioned for example physical agents such as energetic radiation (X-, g- or ultraviolet rays end the like) or chemical agents capable of reacting with various functional groups of the bases of DNA, and for example alkylating agents [ethyl methanesulphonate (EMS), N-methyl-N'-nitro-N-nitrosoguanidine, N-nitroquinoline 1-oxide (NQO)], dialkylating agents, intercalating agents and the like.

Deletion is understood to mean the removal of all or part of the gene considered. This may especially be a portion of the coding region and/or of all or part of the promoter region for transcription.

The genetic modifications can also be obtained by gene disruption, for example according to the procedure initially described by Rothstein (1983). In this case, all or part of the gene is preferably perturbed so as to allow the replacement, by homologous recombination, of the wild-type genomic sequence by a nonfunctional or mutant sequence prepared in vitro.

The said modification(s) may be located in the coding portion of the gene or in the regions responsible for the expression end/or transcriptional regulation of the said genes. The (total or partial) incapacity of the said cells to degrade betaine can manifest itself either by the production of inactive enzymes because of structural or conformational modifications, or by the absence of production, or by the production of enzymes having an impaired activity, or alternatively by the production of natural enzymes at en attenuated level or according to a desired mode of regulation.

Moreover, certain modifications such as point mutations are by nature capable of being corrected or attenuated by cellular mechanisms, for example during the replication of DNA preceding cell division. Such genetic modifications are, in this case, of limited interest at the industrial level since the phenotypic properties resulting therefrom are not perfectly stable. According to the present invention, it is now possible, by virtue of the identification of DNA fragments carrying genes for the catabolism of betaine, to prepare modified cells in which the said modification(s) are segregationally stable and/or nonreversible. The cells exhibiting such modifications are particularly advantageous as cellular host for the production of metabolites end/or enzymes.

In another particular embodiment, the modified cells of the invention are cells in which at least one gene involved in the catabolism of betaine is amplified, and which as a result degrade betaine more rapidly.

The amplification can be obtained by introducing a DNA fragment carrying a gene for the catabolism of betaine into the cell. This fragment is preferably part of a vector, which my be an autonomously replicating vector or an integrative vector. Moreover, the DNA fragment may be homologous or heterologous in relation to the modified cell, that is to say that the amplified gene(s) may be genes from the said cell or genes obtained from other cellular sources and encoding an activity of the same type. The choice of the vector and of the origin of the amplified fragment depends on the cells considered and the applications envisaged. The DNA fragment may be introduced into the cells by any method allowing the introduction of a foreign DNA into a cell. This may be in particular transformation, electroporation, conjugation, protoplast fusion, or any other techniques known to persons skilled in the art.

According to studies carried out essentially in Rizobium meliloti, the degradation of glycine betaine is performed on media of low osmolarity, by three successive demethylations (see FIG. 1). The first stage is catalysed by betaine homocysteine methyltransferase E.C. 2.1.1.5. and leads to dimethylglycine; the second is catalysed by dimethylglycine dehydrogenase E.C. 1.5.99.2 and generates momomethylglycine or sarcosine; finally the third is catalysed by sarcosine dehydrogenase E.C. 1.5.99.1 and the product of the reaction is glycine (Smith et al, 1988).

Preferably, the modifications exhibited by the cells of the invention affect one of the fist two stages of the catabolism of betaine, or optionally the two first stages simultaneously.

Preferably, the cells of the invention are cells which product metabolites and/or enzymes. In this respect, they may also be recombinant cells which product metabolites and/or enzymes, that is to say cells modified by recombinant DNA techniques so as to improve their production capacity (cf. especially WO 91/11518, EP 346000). Still more preferably, the cells of the invention are chosen from cells of the genus Pseudomonas, Streptomyces, actinomycetes, Propionibacterium, Corynabacterium, Bacillus, Escherichia, Salmonella, Rhizobium, Agrobacterium, Rhodopseudomonas, Xanthomonas, Clostridium end Methanobacterium.

Another aspect of the invention relates to a process for preparing cells exhibiting a modification of at least one gene involved in the catabolism of betaine which are capable of being used under industrial fermentation conditions.

The present invention in effect describes the identification, isolation and characterization of DNA fragments containing genes involved in the catabolism of betaine. These fragments now make it possible to prepare cells which are specifically modified with respect to the catabolism of betaine. It is indeed possible to modify in vitro the fragments described so as to make them nonfunctional and to reintroduce them into a given cell, in which they will become substituted by double homologous recombination for the corresponding functional genomic copy. It is also possible, on the basis of the fragments thus isolated, to prepare probes which will become integrated into the genome of a desired cell, specifically in the corresponding gene.

More particularly, the process of the invention consists in replacing the considered chromosomal gene(s) by versions modified in vitro.

Another subject of the invention relates to a DNA fragment carrying at least one gene for the catabolism of betaine.

More particularly, the present invention is illustrated by the isolation and characterization of DNA fragments from Pseudomonas denitrificans which complement the mutants blocked in the catabolism of glycine betaine into dimethylglycine and those blocked in the catabolism of dimethylglycine into sarcosine, that is to say the DNA fragments containing genes involved in the degradation of glycine betaine into dimethylglycine and of dimethylglycine into sarcosine. The DNA fragments according to the invention were isolated from a Pseudomonas denitrificans strain SC510, which is derived from the strain MB580 (U.S. Pat. No. 3,018,225). These fragments were obtained (i) preparation of mutants blocked in the catabolism of betaine. Various techniques already mentioned above can be used to this end. The selection of the is performed by culturing on an appropriate medium and assaying, according to conventional techniques for persons skilled in the art, betaine or products of its acid from a microorganism capable of catabolizing catabolism.

(ii) complementation of three mutants with nucleic betaine, (iii) selection of the complemented mutants, then isolation and characterization of the nucleic acid having allowed this complementation, which therefore carries genes for the catabolism of betaine.

It is clear that, from the DNA fragments identified and isolated in the present application, persons skilled in the art can, especially by hybridization experiments, isolate and clone genes for the catabolism of betaine from other cellular sources.

More preferably, the gene in question is therefore the one encoding betaine-homocysteine methyltransferase, on which gene a modification according to the invention induces, in the cell, a decrease in the betaine-homocysteine methyltransferase activity. Preferably still, the gene in question is the one encoding dimethylglycine dehydrogenase, on which a modification according to the invention induces, in the cell, a decrease in the dimethylglycine dehydrogenase activity.

Another subject of the invention relates to an improved process for producing metabolites or enzymes by culturing a cell which produces the said metabolite or enzyme, modified with respect to its catabolism of betaine, under production conditions, and then recovering the said metabolite or enzyme.

According to a first embodiment, the producing cell exhibits at least one modification with respect to a gene involved in the catabolism of betaine and degrades betaine less rapidly.

Preferably, according to the first embodiment, the modification(s) are segregationally stable and/or nonreversible.

In a preferred variant of the invention, the modification(s) are mutational deletions and/or insertions.

According to a second embodiment, at least one gene of the producing cell, which is involved in the catabolism of betaine, is amplified and the said cell degrades betaine more rapidly.

The process of the invention is particularly suitable for the production of metabolites such as amino acids, vitamins, antibiotics, their derivatives or their precursors.

The process of the invention can especially allow the improved production of cobalamin, and preferably of vitamin B12.

The present invention is supplemented by the following examples which should be considered as illustrative and nonlimiting.

GENERAL MOLECULAR BIOLOGY TECHNIQUES

The methods conventionally used in molecular biology such as preparative plasmid DNA extractions, plasmid DNA centrifugation in a caesium chloride gradient, electrophoresis on agarose or acrylamide gels, purification of DNA fragments by electroelution, phenol or phenol-chloroform extraction of proteins, DNA precipitation in salt medium with ethanol or isopropanol,. transformation in Escherichia coli and the like, are well known to persons skilled in the art and are widely described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

The restriction enzymes were produced by New England Biolabs (Biolabs), or Pharmacia and are used according to the recommendations of the suppliers.

The pBR322 and pUC type plasmids are of commercial origin (Bethesda Research Laboratories).

For the ligations, the DNA fragments are separated according to their size by electrophoresis on agarose or acrylamide gels, exctracted with phenol or with a phenol/ chloroform mixture, precipitated with ethanol and then incubated in the presence of T4 phage DNA ligase (Boehringer) according to the recommendations of the supplier.

The filling of the protruding 5' ends is performed by the Klenow fragment of DNA polymerase I of E. coli according to the specifications of the supplier. The destruction of the protruding 3' ends is performed in the presence of T4 phase DNA polymerase used according to the recommendations of the manufacturer. The destruction of the protruding 5' ends is performed by a controlled treatment with S1 nuclease.

Site-directed mutagenesis in vitro by synthetic oligodeoxynucleotides is performed according to the method developed by Taylor et al. [Nucleic Acids Res. 13 (1985) 8749–8764].

The enzymatic amplification of the DNA fragments by the so-called PCR technique [Polymerase-catalysed Chain Reaction, Saiki R. K. et al., Science 230 (1985) 1350–1354; Mullis K. B. et Faloona F. A., Meth. Enzyme. 155 (1987) 335–350] is performed using a "DNA thermal cycler" (Perkin Elmer Cetus) according to the specifications of the manufacturer.

The verification of the nucleotide sequences is performed by the method developed by Sanger et al. [Proc. Natl. Acad. Sci. U.S.A., 74 (1977) 5463–5467].

ABBREVIATIONS

Betaine: glycine betaine or N,N,N-trimethylglycine
HPLC: high-pressure liquid chromatography
DMG: dimethylglycine
kb: kilobase

LEGEND TO THE FIGURES

FIG. 1: Pathway for the degradation of clycine betaine into glycine. Three successive demethylations take place, the glycine betaine is catabolized into dimethylglycine which is degraded into sarcosine which it itself degraded into glycine.

Figure 2:
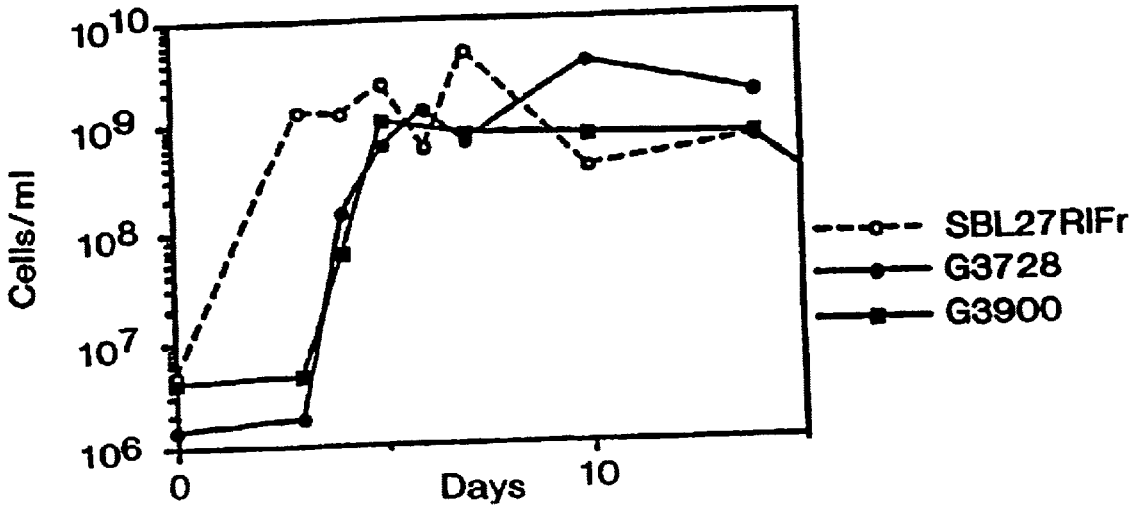

FIG. 2: Growth curve in minimum M medium. The nonmutated SBL27 Rif$^r$ strain and the mutants G3728 and G3900 are cultured in minimum M medium in the presence of glycine betaine as carbon source, their growth is represented on the Y-axis as number of cells per ml, as a function of the time in days described on the x-axis.

Figure 3:
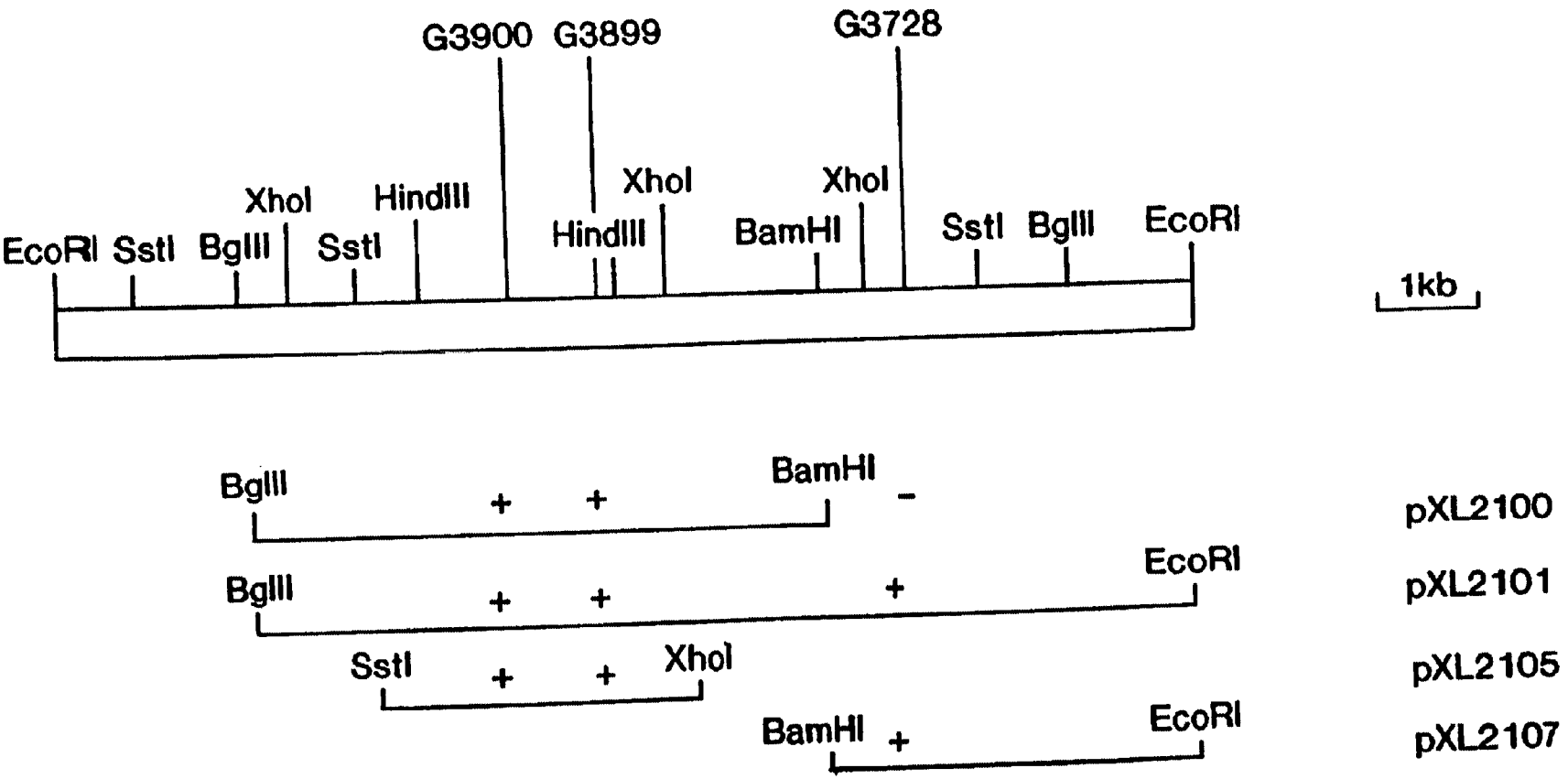

FIG. 3: Mapping of the DNA fragment from P. denitrificans complementing the mutants G3728, G3736, G3899 and G3900. The restriction sites and the position of insertion of the transposon of the corresponding mutants G3728, 33899 end G3900 are indicated on the DNA fragment. The inserts of the plasmids pXL2100, pXL2101, pXL2105 and pXL2107 which were used to complement the mutants are represented below the fragment. + complementation, – no complementation.

Figure 4:
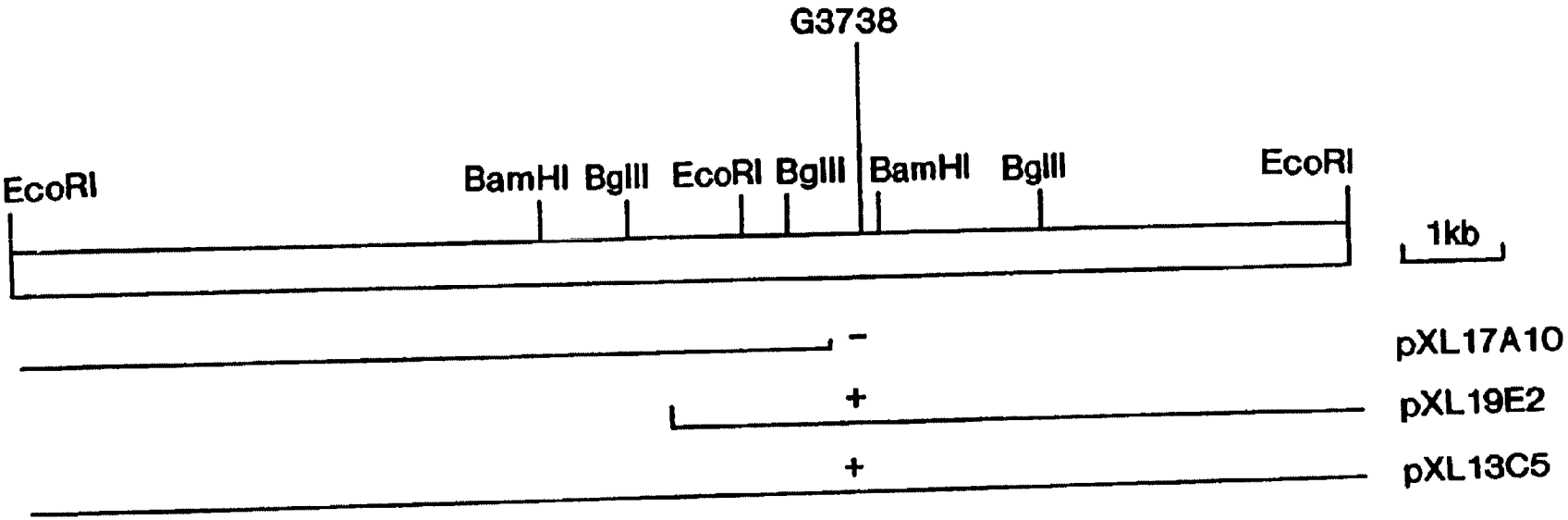

FIG. 4: Mapping of the DNA fragment from P. denitrificans complementing the mutants G3727 and G3738. The restriction sites and the position of insertion of the transposon G3738 are indicated on the DNA fragment. Part of the inserts of the plasmids pXL19E2, pXL17A10, end pXL13C5 which were used to complement the mutants are shown below the fragment. + complementation, + no complementation.

EXAMPLE 1

Isolation of Pseudomonas denitrificans mutants blocked in the catabolism of glycine betaine.

This example describes the isolation of Pseudomonas denitrificans mutants blocked in the catabolism of glycine betaine into dimethylglycine and sarcosine. These mutants were isolated from a library of mutants, in which the transposon Tn5Sp$^r$ is inserted into the genome of the Pseudomonas denitrificans strain SBL27 Rif$^r$. This library was prepared in the following manner: a plasmid, designated pRK2013::Tn5Sp$^r$, was constructed by inserting the spectinomycin resistance gene Sp$^r$ derived from the plasmid pHP45Ω (Prentki et al., 1984) into the BamHI site of the transposon Tn5 (Berg et al., 1983) cloned into the plasmid pRK2013:: Tn5 (Ditta et al., 1980). A conjugation was then performed by mixing the exponential phase cultures of SBL27Rif$^r$ and E. coli MC1060 (pRK1013::Tn5Sp$^r$). The transconjugates Rif$^r$Sp$^r$ were obtained after incubation at 30° C. for 5 days, at the frequency of $10^{-8}$ clones per recipient cell. It was checked for 12 clones that the plasmid introduced had indeed been lost (the plasmid DNA was prepared end then introduced into E. coli by transformation; no clone carrying the resistance of the plasmid was obtained) and that the transposon Tn5Sp$^r$ was indeed integrated into the genome of SBL27Rif$^r$ (by southern as described in Example 2).

About 3000 mutants of this library were reisolated on solid (15 g/l of Difco agar) minimum M medium (1 g/l $NH_4Cl$, 7 g/l $Na_2HPO_4$, 3 g/l $KH_4PO_2PO_4$, 0.5 g/l NaCl, 1 mM $MgSO_4$, 0.1 mM $CaCl_2$, 10 g/l thiamine) where the carbon source is glycine betaine at 10 g/l and then incubated at 30° C. for 3 days. Next, the betaine, the dimethylglycine end the sarcosine were assayed in the culture supernatant after separation Shodex Ionpak S 801 P, length 50 cm, diameter 8 mm; temperature: 70° C.; mobile phase: 0.01M sodium azide) and detection by differential refractometry.

Eighteen mutants were found no longer to use betaine as carbon source, they are 33727 to G3731, G3733 to G3742 and G3897, G3899 and G3900.

Moreover, when these mutants are cultured, according to the procedure already described (Cameron et al, 1989), in 10 ml of PS4 medium for 5 days at 30° C., betaine, or dimethylglycine or sarcosine can be measured in the culture supernatant after separation by HPLC end detection by differential refractometry. Betaine is detected in the broth supernatant of the mutants G3728, G3736, G3897, G3899 and G3900 (between 53 and 98 % of the betaine contained in the initial medium), whereas with the mutants G3727, G3738 and G3742, it is dimethylglycine (about 88 to 97% of the betaine contained in the initial medium); with the mutants G3729, G3730, G3731, G3733, G3737 and G3741, it is sarcosine (about 64 and 75% of the betaine introduced into the medium); with the other mutants G3734, G3735, G3739, G3740 and with the nonmutated strain, none of the three products is observed, see Table 1.

Furthermore, only SBL27 Rif$^r$ and the mutants G3728, G3736, G3897, G3899 and G3900 grow on solid minimum M medium where the carbon source is dimethylglycine (10 g/l). Cultures in liquid minimum M medium where the carbon source is glycine betaine at 10 g/l are performed as follows: starting with a reisolation on rich LB medium (Cameron et al, 1989), the strain is cultured in 5 ml of LB medium at 30° C. for 12 hours; the cells of this preculture are washed in minimum M medium, then inocula of 0.2% are inoculated, in eight Erlenmeyer flasks of 250 ml containing 25 ml of minimum M medium where the carbon source is glycine betaine (10 g/l), and incubated with stirring at 250 rpm, at 30° C. On days 3, 4, 5, 6, 10, 14, 21, the cells contained in an Erlenmeyer flask are counted after plating and growth on solid minimum medium where the carbon source is glycine betaine. When the mutants G3728 and G3900 are cultured in liquid minimum medium where the carbon source is glycine betaine (10 g/l), for the first three days, no growth is observed whereas with the strain SBL27 Rif$^r$ the stationary phase is already reached, see FIG. 2; however, on the sixth day, a stationary phase comparable to that of SBL27 Rif$^r$ is observed. This result shows that the mutants which do not degrade all the betaine (10 g/l) contained in the PS4 medium, see Table 1, are capable of using it, but after a lag phase of 3 days compared with the no-mutated strain, as carbon source in a minimum medium containing 10 g/l of betaine.

These physiological data make it possible to demonstrate in Pseudomonas denitrificans SBL27 Rif$^r$ a pathway for the degradation of glycine betaine into dimethylglycine and sarcosine where:

1) the stage for the degradation of glycine betaine into dimethylglycine is blocked (or partially blocked) in the mutants G3728, G3736, G3897, G3899 and G3900;
2) the stage for the degradation of dimethylglycine into sarcosine is blocked in the mutants G3727, G3738 and G3742;
3) the stage for the degradation of sarcosine is blocked in the mutants G3729, G3730, G3731, G3733, G3737 and G3741.

EXAMPLE 2

Genetic characterization of the Pseudomonas denitrificans mutants blocked in the catabolism of betaine.

This example describes the molecular biology experiments which make it possible to classify and characterize the mutants with the aid of their transposon. The genotype of each mutant is analysed by Southern (Maniatis et al, 1982) in the following manner: the genomic DNA of each mutant (G3727 to G3731, G3733 to G3742 and G3897, G3899 and G3900) was prepared and then all aliquots is digested with the restriction enzyme EcoRI; the fragments thus obtained are separated by electrophoresis on an agarose gel and are then transferred onto a Biodyne membrane; this membrane is then hybridized with one of the following plasmids labelled with $\alpha^{32}$P-dCTP. These plasmids are pT27, pT28, pT30, pT31, pT34, pT35, pT36, pT37, pT38, pT39, pT40, pT42, pT97, pT00. These plasmids were obtained by insertion at the EcoRI site of the vector pRK290 of the unique genomic EcoRI fragment in which is inserted the transposon Tn5Sp$^r$ of the mutants G3727, G3728, G3730, G3731, G3734, G3735, G3736, G3737, G3738, G3739, G3740, G3742, G3897, G3900 respectively. The plasmids pT carrying the desired EcoRI fragment are selected by their resistance to spectinomycin, conferred by the transposon. On hybridizing the membrane for example with the plasmid pT27, the genomic DNA of the mutants G3727 and G3738 shows only one radioactive band corresponding to an EcoRI fragment with a molecular weight of about 16 kb, which indicates that, in these mutants, the transposon is inserted at the same position. In contrast, for the nonmutated strain, the hybridizing fragment is 8 kb and with all the other mutants two fragments hybridize, one comigrates with that of the non-mutated strain and the other has a variable size greater than the size of the transposon (8 kb) (de Bruijn, 1987; Prentki, 1984). The successive hybridizations with each of the plasmids made it possible to group the mutants by classes of hybridization of 1 to 12, see Table 1.

Moreover, the plasmids pT27, pT28, pT30, pT31, pT34, pT36, pT37, pT38, pT97, pT00 were used to reintroduce by double homologous recombination the mutation derived from the insertion of the transposon, into the nonmutated strain SBL27 Rif$^r$, according to a procedure already described (Cameron et al, 1991). For the strains thus obtained by gene disruption, the genotype was checked by Southern as has Just been described in the preceding paragraph, and the phenotype was determined after analysis of the compounds detected in the supernatant of the cultures in PS4 medium as described in Example 1.

For all the strains obtained by gene disruption, which lead to the same phenotype as the initial mutated strains, see Table 1, the quantities of the compounds detected are comparable. These strains belong:

1) either to the hybridization class 5 and accumulate betaine,
2) or to the hybridication class 2 and accumulate dimethylglycine,
3) or to the hybridization class 4 and accumulate sarcosine.

Furthermore, a deletion of a BgIII genomic fragment of 10 kb and insertion of a spectinomycin resistance cassette were carried out using the plasmid pT28. The strain, whose genotype was checked by Southern (as described in the first paragraph of this example) has the same betaine accumulation phenotype as the strains described in the hybridization class 5.

TABLE 1

Clarification of the mutants blocked in the catabolism of betaine into sarcosine.

| Strains | | Compounds detected in the strains | |
|---|---|---|---|
| No. G | Hybridization classes | initial mutants | genetic disruptants |
| 3727 | 2 | DMG 88% | DMG |
| 3728 | 5 | Betaine 53% sarcosine 13% | Betaine |
| 3729 | 3 | Sarcosine 68% | ND |
| 3730 | 3 | Sarcosine 69% | 0 |
| 3731 | 4 | Sarcosine 64% | Sarcosine |
| 3733 | 4 | Sarcosine 69% | ND |
| 3734 | 7 | 0 | 0 |
| 3735 | 8 | 0 | ND |
| 3736 | 1 | Betaine 62% | 0 |
| 3737 | 4 | Sarcosine 75% | Sarcosine |
| 3738 | 2 | DMG 91% | DMG |
| 3739 | 9 | 0 | ND |
| 3740 | 10 | 0 | ND |
| 3741 | 4 | Sarcosine 64% | ND |
| 3742 | 11 | DMG 97% | ND |
| 3897 | 12 | Betaine 96% | 0 |
| 3899 | 5 | Betaine 95% | ND |
| 3900 | 5 | Betaine 98% | Betaine |

EXAMPLE 3

Complementation of Pseudomonas denitrificans mutants blocked in the stages for demethylations of glycine betaine into sarcosine.

This example describes the isolation of DNA fragments from P. dentrificans carrying genes involved in the degradation of betaine into sarcosine. These fragments were detected by hybridization experiments, using the insert of the plasmids pT28 or pT38 as probe and the library of plasmids containing Sau3AI fragments of the P. denitrificans DNA which are cloned into pXL59 (Cameron et al, 1989). The inserts of the plasmids hybridizing with the probe were mapped. Clones and subclones, which were constructed (Maniatis et al, 1982) in the vectors derived from RSF1010 (Cameron et al, 1989), were introduced by conjugation (Cameron et al, 1989) in the mutants blocked in the catabolism of betaine into dimethylglycine or in the mutants blocked in the degradation of dimethylglycine into sarcosine. The complementation of the mutants by the clones or the subclones was determined by the absence of accumulation of betaine, dimethylglycine or sarcosine in the culture supernatant of the transconjugant strains cultured in PS4 medium, as described in Example 1. 3-1 DNA fragment from P. denitrificans carrying genes involved in the degradation of betaine into dimethylglycine.

The clones hybridizing with pT28, were introduced into the mutants G3728, G3736, G3897, G3899 and G3900 blocked in the catabolism of betaine into dimethylglycine. As is presented in FIG. 3, two subclones pXL2105 and pXL2107 contained in the EcoRI fragment of 12 kb complement four mutants among the five G3728, G3736, G3899 and G3900. One of the subclones pXL2105 contains a 3.4 kb SstI-XhoI fragment cloned into the vector pXL435 (Cameron et al, 1989) and complements two mutants G3900 and G3899; the other pXL2107 contains a 4 kb BamHI-EcoRI fragment cloned into pKT230 (Cameron et al, 1989) and complements the mutants G3728 and G3736. Moreover, the insertion of the transposon in the mutants G3728, G3899 and G3900 has indeed beam mapped on this 12 kb EcoRI fragment, which is not observed in the mutant G3736. It is possible that the phenotype of this mutant is not correlated with the position of the transposon since the mutant obtained after reverse genetics does not accumulate betaine, see Example 2. Consequently, at least two genes are involved in the stage for degradation of betaine into dimethylglycine. 3-2 DNA fragment from P. denitrificans carrying genes involved in the degradation of dimethylglycine into sarcosine.

The clones hybridizing with pT38 were introduced into the mutants G3727, G3738 blocked in the catabolism of dimethylglycine into sarcosine. As is presented in FIG. 4, two clones derived from the library and mapping on a 14.5 kb EcoRI-EcoRI-EcoRI fragment complements G3727 and 33738. One of the subclones pXL19E2 contains a 6.6 kb EcoRI fragment and the other pXL13C5 contains the 14.5 kb EcoRI-EcoRI-EcoRI fragment. Consequently, at least one gene, mapped on the fragment described in FIG. 4, is involved in the stage for degradation of dimethylglycine into sarcosine.

EXAMPLE 4

Improvement of the production of vitamin $B_{12}$ in a Pseudomonas denitrificans strain modified in the catabolism of glycine betaine.

This example illustrates the improvement in the production of cobalamins in a cobalamin-producing strain by disruption of genes involved in the catabolism of betaine into dimethylglycine.

The mutation, which is responsible for the phenotype of the mutant G3728 (or G3900), is generated by the transposon which is mapped on the EcoRI fragment, cloned into pT28 (or pT00) and described in Example 2. This mutation was introduced by double homologous recombination into the cobalamin-producing P. denitrificans strain SC510 Rif$^r$ (Cameron et al, 1991). For both strains thus obtained SC510 Rif$^r$::pT28 and SC510 Rif$^r$::pT00 by reverse genetics, the genotype was checked by Southern as described in Example 2, and the production of cobalamins was determined after analysis by HPLC (column: Asahibak OD50, length: 15 cm, diameter: 6 mm, mobile phase: acetonitrile/0.1M potassium cyanide) and ultraviolet detection (wavelength: 365 nm) of the vitamin $B_{12}$ contained in cultures of the strains grown for seven days at 30° C. in 250 ml Erlenmeyer flasks containing 25 ml of PS4 medium where the betaine glycine is at 2 mg/l, according to a procedure already described (Cameron et al, 1989). The results of these assays are indicated in Table 2. They represent the mean value obtained for two cultures in the four experiments performed independently.

Under the culture conditions used, the production of cobalamins is increased by a factor of 10, compared with the SC510Rif$^r$ strain, in the mutated strains in an EcoRI genomic fragment of 13 kb, see FIG. 3, whose DNA encodes genes involved in the catabolism of betaine into dimethylglycine. These results show clearly that by modifying the catabolism of the betaine of the strains of the invention, their metabolite-producing capacity has been increased. Table 2. Production of vitamin $B_{12}$ in the strains mutated in the EcoRI fragment carrying genes involved in the catabolism of betaine into dimethylglycine. The levels of production of the modified strains are given relative to the production of the Sc510 Rif$^r$ strain, which was arbitrarily set at 1.

| Strains/experiment | 1 | 2 | 3 | 4 |
|---|---|---|---|---|
| Sc510 Rif' | 1 | 1 | 1 | 1 |
| SC510 RifnpT28 | 10.5 | 11 | 22 | 14.5 |
| SC510 RifnPT00 | 11 | 8 | | |

BIBLIOGRAPHIC REFERENCES

Berg D. et al., 1983, Bio/Technology 1: 417–435 F. de Bruijn. 1987. Methods in Enzymology. 154: 175–156.

B. Cameron, K. Briggs, S. Pridmore, G. Brefort and J. Crouzet. 1989. J. Bacteriol. 171: 547–557.

B. Cameron, C. Guilhot, F. Blanche, L. Cauchois, M. Rouyez, S. Rigault, S. Levy-Schil and Crouzet. 1991. J. Bacteriol. 173: 6058–6065.

S. Cayley, B. Lewis and T. Record. 1992. J. Bacteriol. 174: 1586–1595.

L. Csonka. 1989. Microbiol. Rev. 53: 121–147.

Ditta, G. et al., 1980, Proc. Natl. Acad. Sci. U.S.A. 77: 7347–7351.

J. Graham and B. Wilkinson. 1992. J. Bacteriol. 174: 2711–2716.

T. Maniatis, E. Fritsch and J. Sambrook. 1982. Molecular cloning: a laboratory manual. Cold Spring Harbor Laboratory, Cold Spring Harbor, N.Y.

A. Oren. 1990. Antonie van Leeuwenhoek 58: 291–298.

P. Prentki and H. Krisch. 1984. Gene. 29: 303–313.

Rothstein 1983, Meth. Enzymol. 101 202.

L. Smith, J. Pocard, T. Bernard, D. Le Rudulier. 1988. J. Bacteriol. 170: 3142–3149.

R. White and A. Demain. 171. Biochim. Biophys. Acta. 237: 112–119.

We claim:

1. A process for the production of metabolites or enzymes or both comprising a) genetically modifying a cell by gene disruption, wherein said disruption causes at least one stable or nonreversible modification in a gene encoding a protein involved in the catabolism of glycine-betaine; and b) culturing said cell under production conditions.

2. The process according to claim 1, wherein the modified cell degrades betaine less rapidly than an unmodified cell.

3. The process according to claim 2, wherein the modification affects the coding portion of said gene [and/or] *or* the regions responsible for the expression [and/or] *or* the transcriptional regulation of said gene.

4. The process according to claim 2, wherein the cell is of a genus selected from the group consisting of Pseudomonas, Streptomyces, Actinomycetes, Propionibacterium, Corynebacterium, Bacillus, Escherichia, Salmonella, Rhizobium, Agrobacterium, Rhodopseudomonas, Xanthomonas, Clostridium and Methanobacterium.

5. The process according to claim 2, wherein the metabolite is selected from the group consisting of (a) amino acids, (b) vitamins, (c) antibiotics, (d) a derivative of (a), (b) or (c), and (e) a precursor of (a), (b) or (c).

6. The process according to claim 5, characterized in that the metabolite is vitamin B12.

7. The process according to claim 1, wherein the cell is of a genus selected from the group consisting of Pseudomonas, Streptomyces, Actinomycetes, Propionibacterium, Corynebacterium, Bacillus, Escherichia, Salmonella, Rhizobium, Agrobacterium, Rhodopseudomonas, Xanthomonas, Clostridium and Methanobacterium.

8. The process according to claim 1, wherein the metabolite is selected from the group consisting of (a) amino acids, (b) vitamins, (c) antibiotics, (d) a derivative of (a), (b) or (c), and (e) a precursor of (a), (b) or (c).

9. The process according to claim 8, characterized in that the metabolite is a cobalamin.

10. The process according to claim 8, wherein the metabolite is vitamin B12.

11. The process according to claim 1, wherein said gene encodes an enzyme selected from the group consisting of betaine homocysteine methyltransferase, dimethylglycine dehydrogenase, and sarcosine dehydrogenase.

12. The process according to claim 11, wherein said enzyme is betaine homocysteine methyltransferase.

13. The process according to claim 11, wherein said enzyme is dimethylglycine dehydrogenase.

14. A process according to claim 1, wherein the step of gene disruption comprises insertion of a transposon.

15. A process according to claim 1, wherein the step of gene disruption comprises homologous recombination.

16. A recombinantly modified cell comprising at least one stable or nonreversible modification in a gene encoding a protein involved in the catabolism of glycine-betaine, wherein said modification is a gene disruption.

17. The recombinantly modified cell according to claim 16, wherein said gene encodes an enzyme selected from the group consisting of betaine homocysteine methyltransferase, dimethylglycine dehydrogenase, and sarcosine dehydrogenase.

18. The recombinantly modified cell according to claim 17, wherein said enzyme is betaine homocysteine methyltransferase.

19. The recombinantly modified cell according to claim 17, wherein said enzyme is dimethylglycine dehydrogenase.

20. A cell according to claim 16, wherein said gene disruption comprises an insertion.

*21. A process for the production of metabolites or enzymes or both, comprising culturing the recombinantly modified cell according to claim 16 under production conditions.*

*22. The process according to claim 21, wherein said gene encodes an enzyme selected from the group consisting of betaine homocysteine methyltransferase, dimethylglycine dehydrogenase, and sarcosine dehydrogenase.*

*23. The process according to claim 22, wherein said enzyme is betaine homocysteine methyltransferase.*

*24. The process according to claim 22, wherein said enzyme is dimethylglycine dehydrogenase.*

*25. The process according to claim 21, wherein said gene disruption comprises an insertion.*

* * * * *